United States Patent [19]
Bolk et al.

[11] Patent Number: 5,357,551
[45] Date of Patent: Oct. 18, 1994

[54] X-RAY ANALYSIS APPARATUS WITH PULSE AMPLITUDE SHIFT CORRECTION AND DETECTOR READING CIRCUIT MEANS SUITED FOR USE IN SUCH AN APPARATUS

[75] Inventors: Hendrik J. J. Bolk; Georges C. P. Zieltjens, both of Almelo, Netherlands

[73] Assignee: U.S. Philips Corporation, New York, N.Y.

[21] Appl. No.: 48,087

[22] Filed: Apr. 15, 1993

[30] Foreign Application Priority Data

Apr. 15, 1992 [EP] European Pat. Off. ........ 92201072.3

[51] Int. Cl.$^5$ .......................................... G01N 23/223
[52] U.S. Cl. .......................................... 378/98; 378/49
[58] Field of Search ................. 378/44, 49, 98, 45, 378/53, 86, 88, 91

[56] References Cited

U.S. PATENT DOCUMENTS

| | | | |
|---|---|---|---|
| 3,790,792 | 2/1974 | Ishijima | 378/49 |
| 4,121,098 | 10/1978 | Jagoutz et al. | 378/49 |
| 4,546,488 | 10/1985 | Kleefstra . | |

FOREIGN PATENT DOCUMENTS

| | | | |
|---|---|---|---|
| 0090465 | 10/1983 | European Pat. Off. . | |
| 0093048 | 7/1980 | Japan | 378/49 |

OTHER PUBLICATIONS

"Principles and Practice of X-Ray Spectrometric Analysis", by E. P. Bertin, Plenum Press, New York, London, pp. 342–351.

*Primary Examiner*—David P. Porta
*Attorney, Agent, or Firm*—Jack D. Slobod

[57] ABSTRACT

In a gas ionization x-ray detector pulse-amplitude shifts will adversely affect the accuracy of the analysis. At increasing count rates a space charge building up leads to a decrease of the impact ionization in the detector thereby causing the detected pulse amplitude to become lower. By means of addressing a pulse-shift correction random-access memory with digital signals representing detected pulse amplitudes count rates pertaining to high-energy parts and low-energy parts, respectively of a peak in a pulse-height distribution are generated. A difference of count rates for a high-energy part and for a low-energy part of the same peak in the pulse-height distribution indicates pulse-amplitude shift. On the basis of the differences of the high-energy count rate and the low-energy count rate a correction signal is produced for adjusting the amplification of the pulse-amplitudes. To obtain stable operation pulse-shift correction is activated only when the count rate exceeds a threshold value.

16 Claims, 2 Drawing Sheets

X-RAY ANALYSIS APPARATUS WITH PULSE AMPLITUDE SHIFT CORRECTION AND DETECTOR READING CIRCUIT MEANS SUITED FOR USE IN SUCH AN APPARATUS

BACKGROUND OF THE INVENTION

1. Field of the Invention

The invention pertains to an x-ray analysis apparatus comprising an x-ray source, a sample holder, an x-ray detector with pulse counting amplification means and gain control means being controlled by a correction signal, and detector reading circuit means. The invention also relates to detector reading circuit means for performing pulse amplitude shift correction.

2. Description of the Related Art

An x-ray analysis apparatus of said kind is described in the European Patent EP 0 090 465 which corresponds to commonly owned U.S. Pat. No. 4,546,488.

In the x-ray analysis apparatus described in the cited reference, circuitry is provided for automatic correction of pulse amplitude shifts. However, said circuitry is suitable only for application in conjunction with single-channel pulse analyzing means.

SUMMARY OF THE INVENTION

It is inter alia an object of the invention to provide an x-ray analysis apparatus having automatic pulse amplitude shift correction in conjunction with multi-channel pulse analysis for automatic correction of positioning pulse height distributions.

To achieve this, an x-ray analysis apparatus in accordance with the invention is characterised in that the x-ray analysis apparatus comprises an analog-to-digital converter for convening analog pulse-amplitudes produced by the detector into digital signals, and in that the detector reading circuit means comprises an address-to-data conversion means for producing pulse-frequency signals, and comprises pulse-frequency signal comparison means for producing correction signals in correspondence with differences between said pulse-frequency signals.

In particular in a gas ionisation x-ray detector comprising a gas-filled detector cell pulse amplitude shifts occur when the count rate increases. As it is discussed in 'Principles and practice of x-ray spectrometric analysis', 2nd ed. by E. P. Bertin, Ch. 8.1.8, pulse amplitude shifts are predominantly due to variations in the natural amplification of the x-ray gas ionisation detector, but can also result from thermal drift. At increasing count rates, i.e. increasing x-ray intensity, the pulse-height distribution shifts to lower average pulse-height. That is, at increasing count rates a seemingly decreasing energy of incident x-ray photons is measured. Albeit to a lesser extent as compared to gas ionisation detectors alternative x-ray detectors such as semiconductor x-ray detectors or scintillation x-ray detectors also suffer from pulse amplitude shifts at increasing count rates.

A preferred embodiment of an x-ray analysis apparatus in accordance with the invention is characterised in that the address-to-data conversion means comprises one of several alternative components: a pulse-shift random access memory, or a pulse-shift-correction programmable read-only memory, or a programmable logical circuit.

Pulse amplitude shifts are detected by comparing a high-energy part to a low-energy part of a peak in a pulse-height distribution. A difference in count rates pertaining to a low-energy part and to a high energy part, respectively, of a peak in a pulse-height distribution indicates a pulse-amplitude and a difference between said count rates provides a correction signal for adjusting the pulse-counting amplification by means of the gain control circuit. Count rates pertaining to high-energy parts and to low-energy parts in a peak in a pulse-height distribution are formed from count rates in relevant channels by way of connecting relevant channels pertaining to high-energy parts and to low-energy parts, respectively, of a peak in a pulse-height distribution, to relevant datalines. To that end an address-to-dam conversion means, comprising address-lines and dam-lines, for convening signals incident at groups of addresses into signals exiting at datalines. This can be achieved electronically by means of several alternative components such as a pulse-shift-correction random access memory, or a pulse-shift-correction programmable read-only memory, or a programmable logical circuit.

A preferred embodiment of an x-ray analysis apparatus in accordance with the invention is further characterised in that said pulse-frequency comparison means comprises two frequency-to-amplitude converters and a differential integrator.

Comparison of pulse-frequency signals is carded out in the present preferred embodiment by convening said pulse-frequency by means of a first and a second frequency-to-amplitude converter into signal amplitudes and subsequently subtracting said signal amplitudes by means of a differential integrator. An output signal produced by the differential integrator is equal to a difference of signal amplitudes generated by a the first and second frequency-to-amplitude converter, respectively. Said output signal of the differential amplifier is employed as a correction signal for the gain control circuit.

A further preferred embodiment of an x-ray analysis apparatus in accordance with the invention is characterised in that said pulse-frequency comparison means comprises a first counter operating in an ascending way, a second counter operating in a descending way and an integration circuit.

Comparison of pulse-frequency signals is carried out digitally in the present preferred embodiment by converting said pulse-frequency by means of a first and a second counter into counts, the first counter counting ascendingly, the second counter descendingly and subsequently forming a difference of said counts by means of an integration circuit. An output signal produced by the integration circuit is equal to a difference of counts generated by a the first and second counter, respectively. Said output signal of the differential amplifier is employed as a correction signal for the gain control circuit.

A further preferred embodiment of an x-ray analysis apparatus in accordance with the invention is characterised in that the detector reading circuit means comprises a count rate switch for activating said pulse-frequency signal comparison means in dependence of said pulse-frequency signals exceeding a threshold.

When an x-ray analysis is performed for an energy range where only low count rates are produced by the detector, then there pulse amplitude shifts are absent, because at low rates of incidence of x-ray photons no weakening by space charges occurs of the applied electric field in the gas ionisation detector. Moreover, applying pulse amplitude shift correction at low count rates has as a drawback that operation of the x-ray analysis apparatus becomes unstable. Therefore, a preferred embodiment of an x-ray analysis apparatus in accordance with the invention comprises a count rate switch for activating pulse shift correction when the count rate exceeds a predetermined value.

A further preferred embodiment of an x-ray analysis apparatus in accordance with the invention is characterised in that the analog-to-digital converter is a Flash-analog-to-digital converter.

For satisfactory operation at high count rates the time that is consumed by converting the analog signal amplitudes generated by the detector into digital signals is preferably reduced. This is achieved by employing a Flash-analog-to-digital converter for rapidly converting analog signal amplitudes generated by the detector into digital signals.

A detector reading circuit means suited for automatic performing pulse-amplitude shift correction of a pulse-height distribution preferably comprises a address-to-data conversion means for producing pulse-frequency signals and pulse-frequency signal comparison means for producing correction signals in correspondence with differences between said pulse-frequency signals.

These and other aspects of the invention will become apparent from and elucidated with reference to the embodiments described hereinafter and with reference to the accompanying drawing.

DETAILED DESCRIPTION OF THE PREFERRED EMBODIMENTS

Figure 1:
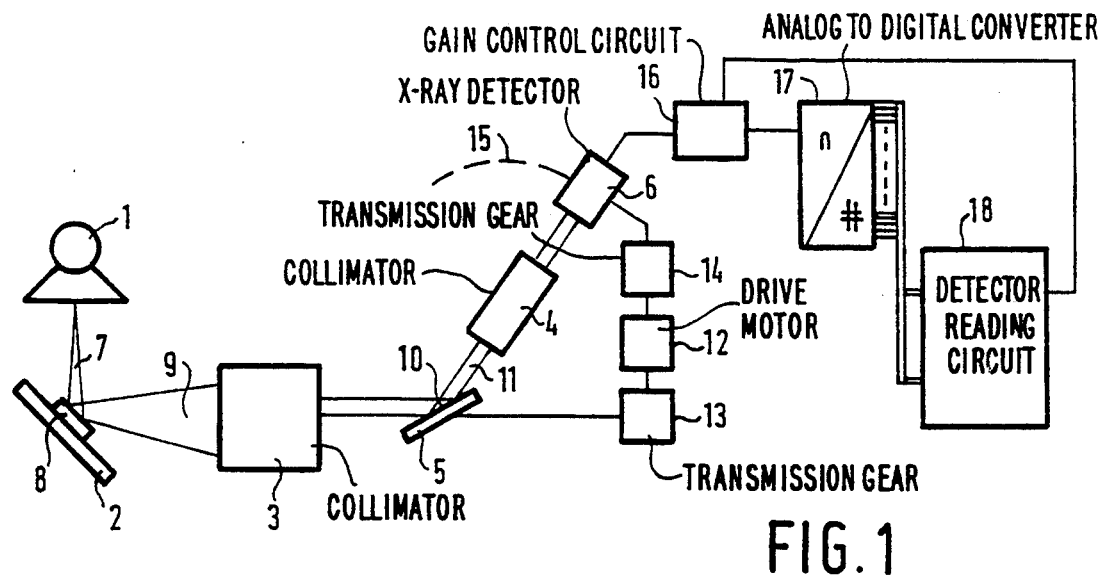
FIG. 1 shows diagrammatically an x-ray analysis apparatus employing multi-channel pulse analysis and having automatic pulse amplitude shift correction of a pulse-height distribution.

An x-ray analysis apparatus shown in FIG. 1 comprises an x-ray source 1, a sample holder 2, collimators 3 and 4, an analyzing crystal 5 and an x-ray detector 6. Notably, the x-ray detector 6 is a gas ionisation detector. An x-ray beam 7 is incident on a sample 8 and causes x-ray fluorescence to be emitted by the sample. A fluorescence x-ray beam 9 is incident via the collimator 3 on a surface 10 of the analyzing crystal 5, after which a further x-ray beam 11 reflected according to Bragg reflection therefrom reaches the x-ray detector 6 via the collimator 4. By way of a drive motor 12 and a transmission gear 13 the analyzing crystal is at option rotated about an axis perpendicular to the plane of the drawing. By means of this rotation the energy of the x-ray beam incident on the x-ray detector is selected within a narrow range. The motor 12, acting via a transmission gear 14, causes a rotation of the detector which matches the rotation of the crystal, likewise about an axis at right angles to the plane of the drawing. Due to this rotation, the detector is moved along an arc of a circle 15. The analog signal amplitudes generated by the detector are controlled by a gain control circuit 16. Subsequently said analog signal amplitudes generated by the detector are converted into a digital representation by an analog-to-digital converter 17. The signal amplitude of a signal generated by the detector is in correspondence with an energy of an x-ray photon incident on the detector. Thus, a frequency distribution of amplitudes of signals generated by the detector corresponds to an energy distribution of x-ray photons incident on the detector. Said frequency distribution of amplitudes of signals will be referred to hereinafter as a pulse-height distribution. The digital signal from the analog-to-digital converter 17 is processed by detector reading circuit means 18 that will be further discussed hereinafter with reference to FIGS. 3a and 3b.

Figure 2:
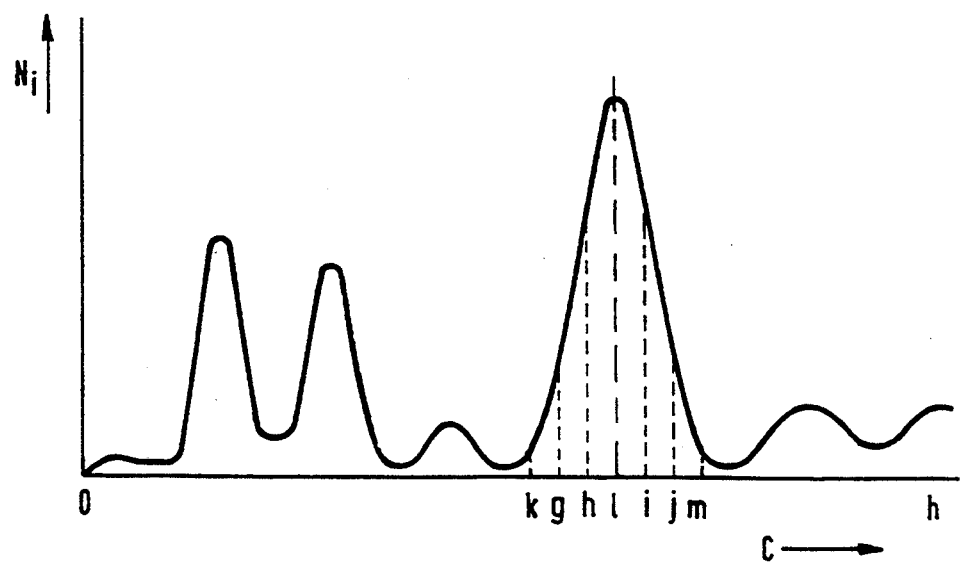
FIG. 2 shows an example of a pulse-height distribution to be measured.

In FIG. 2 an example of a pulse height distribution is shown. As a function of count rate C, the number $N_i$ of pulses corresponding to said energy is shown.

Figure 3A:
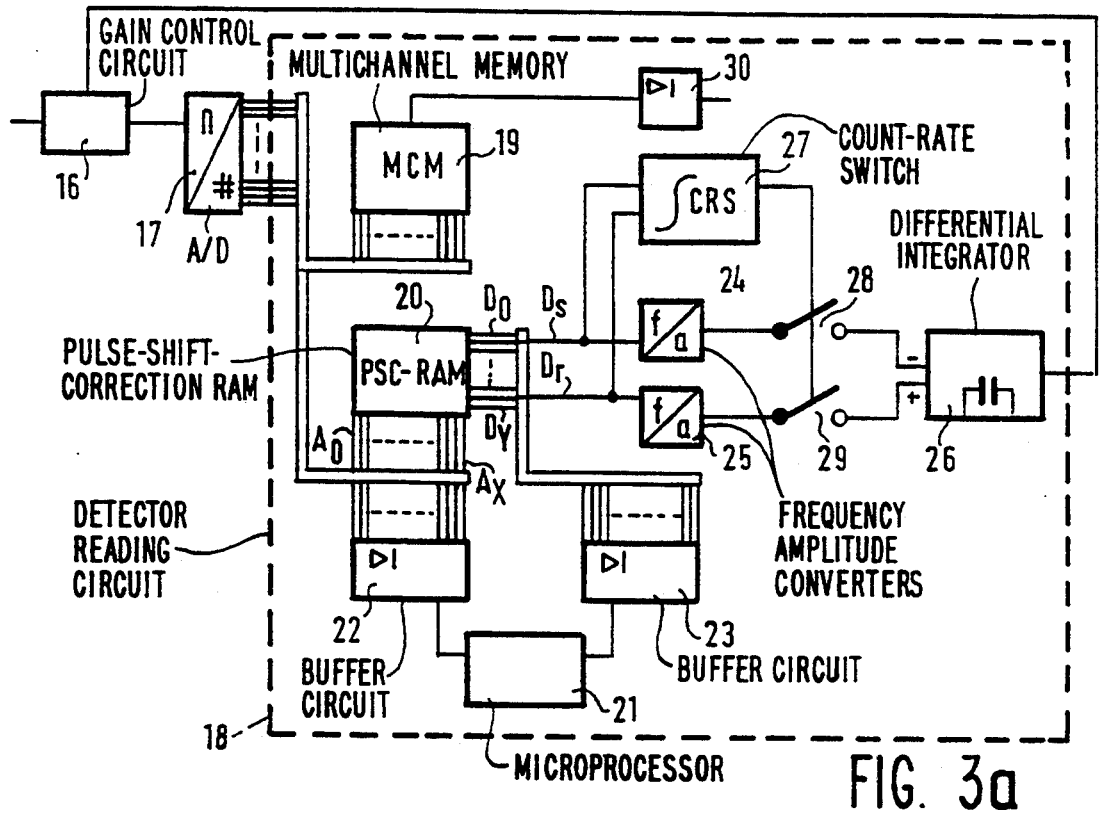
FIG. 3a shows a block diagram of an embodiment of a circuit for automatic pulse amplitude shift correction.

FIG. 3a shows a more detailed block circuit diagram of an embodiment of a detector reading circuit for an x-ray analysis apparatus in accordance with the invention. A digital signal provided by the analog-to-digital converter 17 is supplied to a multi-channel memory 19. For high-speed operation of the detector reading circuit, the analog-to-digital converter is a Flash-ADC. A channel number of the multi-channel memory corresponds to a narrow range of values for signal amplitudes of signal amplitudes generated by the detector; the width of said range being determined by the ratio of a predetermined width of a range of x-ray energies relevant for performing an x-ray analysis to a number of channels of the multi-channel memory. Tendering a digital signal to the multi-channel memory has as an effect that a value stored in a relevant channel of the multi-channel memory is increased by one unit, the relevant channel being in correspondence with the amplitude of the signal generated by the detector. Correspondingly, a channel number of the multi-channel memory corresponds to a narrow range of values of energies of x-ray photons detected by the x-ray detector. Said digital signal is also provided to the addressing lines of the pulse-shift-correction random access memory (PSC-RAM) 20, the PSC-RAM comprising addressing lines indicated as $A_0$–$A_X$ and comprising datalines indicated as $D_0$–$D_Y$. The PSC-RAM is programmed so as to correlate groups of addressing lines with predetermined datalines. The programming of the PSC-RAM is performed using a micro-processor 21 that is to be connected to the detector reading circuit for programming the PSC-RAM, indicating addresses by way of a first buffer circuit 22 and supplying dam by means of a second buffer circuit 23. As an example, the PSC-RAM is programmed as follows:

Addresses in the range $A_0$–$A_k$ relate to datalines $D_r$ and $D_s$, datalines $D_r$ and $D_s$ both containing the value 0. That is, whenever signals are supplied to addresses in the range $A_0$–$A_k$, none of the datalines $D_r$ and $D_s$ produces a signal.

Addresses in the range $A_k$–$A_l$ relate to datalines $D_r$ and $D_s$, data-line $D_r$ containing the value 1 and $D_s$ containing the value 0. That is, whenever signals are supplied to addresses in the range $A_k$–$A_l$, a short (e.g. approximately 50 ns) signal pulse of a predetermined amplitude is produced by dam-line $D_r$ and no signal is produced by dam-line $D_s$.

Addresses in the range $A_l$–$A_m$ relate to datalines $D_r$ and $D_s$, data-line $D_r$ containing the value 0 and $D_s$ containing the value 1. That is, whenever signals are supplied to addresses in the range $A_l$–$A_m$, a short (e.g. approximately 50 ns) signal pulse of a predetermined amplitude is produced by data-line $D_s$ and no signal is produced by data-line $D_r$.

Addresses in the range $A_m$–$A_h$ relate to datalines $D_r$ and $D_s$, datalines $D_r$ and $D_s$ both containing the value 0. That is, whenever signals are supplied to addresses in the range $A_m$–$A_h$, none of the datalines $D_r$ and $D_s$ produces a signal.

The addresses $A_o$ and $A_h$ correspond to channels relating the lowest and to the highest x-ray energy, respectively that are present in a relevant spectral range. The address $A_l$ corresponds to a channel relating to an energy where a pulse-height distribution at issue has a local maximum, i.e. an energy corresponding substantially to a centre of a peak in a pulse-height distribution. The energies at edges of a peak for which the address $A_l$ corresponds to a centre correspond to addresses $A_k$ and $A_m$, respectively.

The operation of pulse-shift correction for the pulse height distribution by an embodiment of an x-ray analysis apparatus in accordance with the invention can now be further discussed. Tendering a digital signal to the PSC-RAM has as an effect that signal pulses are produced by datalines $D_r$ and $D_s$. The rate of signal pulses produced by datalines $D_r$ and $D_s$ correspond to the rate of incidence of x-ray photons having energies pertaining to addressing lines in the ranges $A_k$–$A_l$, and $A_{l+1}$–$A_m$, respectively. That is, datalines $D_r$ and $D_s$ produce pulse-frequency signals in correspondence with integrated pulse rates in a low-energy and in a high-energy part of a peak in the pulse-height distribution; said peak being determined by selection of addressing lines $A_k, A_l$ and $A_m$. Output thus provided by the PSC-RAM will be called pulse-frequency signals hereinafter. Said pulse-frequency signals provided by datalines $D_r$ and $D_s$, respectively are converted into signal amplitudes, notably voltages, by way of frequency-to-amplitude converters 24, 25. Said signal amplitudes are subsequently subtracted from one another by means of a subtraction means, notably a differential integrator 26. Finally, said differential integrator provides a correction signal for adjusting amplification of signals generated by the detector, by means of the gain control circuit 16 in accordance to the frequency signals from the first frequency-to-amplitude converter 24 and from the second frequency-to-amplitude converter 25, respectively, being substantially different.

In another mode of operation of an embodiment of a detector reading circuit suited for an x-ray analysis apparatus in accordance with the invention, pulse-frequency signals are formed pertaining to count-rates of a high-energy portion and a low-energy portion being non-adjacent to each other, of a peak in the pulse-height distribution. To that end, the PSC-RAM 20 is programmed such that addresses in the range of $A_g$ and $A_h$ relate to data lines $D_r$ and $D_s$, dataline $D_r$ containing the value 1, dataline $D_s$ containing the value 0, and addresses in the range $A_i$ and $A_j$ relate to datalines $D_r$ and $D_s$, dataline $D_r$ containing the value 0, dataline $D_s$ containing the value 1. Upon tendering a digital signal to the PSC-RAM 20, data lines $D_r$ and $D_s$ produce pulse-frequency signals corresponding to integrated pulse-rates in portions of a pulse-height distribution at issue, said portions being determined by selection of addressing lines $A_g$, $A_h$, $A_i$, $A_j$. Said portions are preferably chosen symmetrically around a load maximum in the pulse-height distribution; however the present embodiment is suited for more sophisticated selections of addressing lines $A_g$, $A_h$, $A_i$, $A_j$ depending on detailed shapes of peaks in the pulse-height distribution.

When signal amplitude from the first frequency-to-amplitude converter 24 is larger than a corresponding signal amplitude from the second frequency-to-amplitude converter 25, this is caused by a shift to lower energy of the pulse-height distribution. Then the differential integrator 26 provides a positive signal which causes, by way of the gain control circuit 16, to increase the amplification until the signal amplitudes generated by the first and second frequency-to-amplitude converters, respectively, have become equal. Then correspondingly, the pulse amplification is adjusted so that the count rates in a low-energy half and in a high-energy half of a relevant peak in a pulse-height-distribution are substantially equal.

Pulse-shift correction is both unnecessary and undesired when a count rate is lower than some predetermined level. In order to activate pulse-shift correction only when a count rate exceeds some predetermined level, an x-ray analysis apparatus in accordance with the present invention is provided with a count-rate-switch 27. The selection of whether or not performing pulse-shift correction is performed as follows. Frequency signals from the datalines $D_r$ and $D_s$ are supplied to the count-rate-switch. Provided one of said frequency signals exceeds some first predetermined threshold value then switches 28,29 are closed, so that the frequency-to-amplitude converters are connected to the differential integrator. Once the switches 28,29 have been closed, they remain closed unless both frequency signals from the datalines $D_r$ and $D_s$ decrease below some second predetermined threshold value, the second predetermined threshold value being lower than the first predetermined threshold value. When both frequency signals decrease below said predetermined second threshold value, then the switches 28,29 are opened. This mode of operation the count rate switch avoids unstable behaviour of the pulse-shift correction. Output of the pulse-height distribution produced by the x-ray analysis apparatus is carried out by way of an output buffer circuit 30.

Figure 3B:
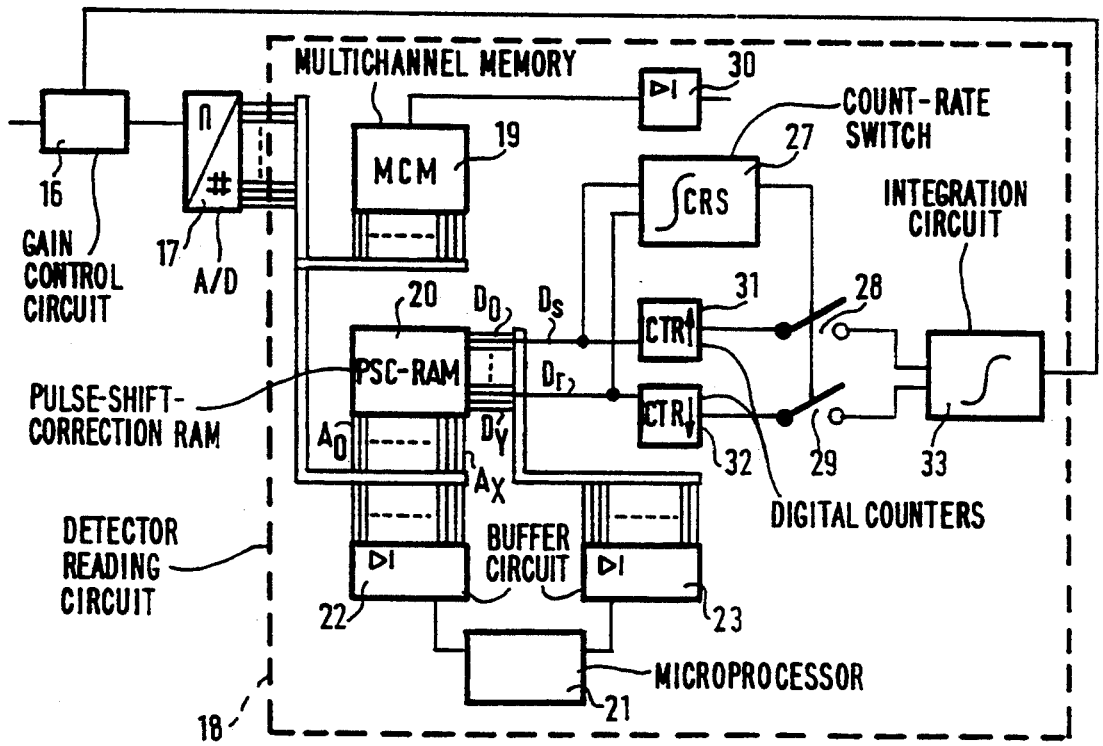
FIG. 3b shows a block diagram for another embodiment of a circuit for automatic pulse amplitude shift correction.

FIG. 3b shows another embodiment of a circuit for automatic pulse amplitude shift correction. In the embodiment according to FIG. 3b the relevant datalines $D_r$ and $D_s$ of the PSC-RAM 20 are connected to respective digital counters 31 and 32. Counter 31 operates so as to count incoming pulses from the PSC-RAM in an ascending way. Counter 32 operates so as to count incoming pulses from the PSC-RAM is a descending way. The counters 31 and 32 are connected to an integration circuit 33 which supplies a signal to the gain control signal. The count rate switch controls switches 28 and 29 for connecting the counters 31 and 32 with the integration circuit in dependence of pulse-frequencies supplied by the relevant datalines of the PSC-RAM.

We claim:

1. An x-ray analysis apparatus comprising an x-ray source, a sample holder, an x-ray detector with pulse counting amplification means and gain control means being controlled by a correction signal, an analog-to-digital converter for converting analog pulse-amplitudes produced by said x-ray detector into digital signals, and detector reading circuit means comprising an address-to-data conversion means for receiving said digital signals as addresses and for producing pulse-frequency signals as data in response to said addresses, and pulse-frequency signal comparison means for producing correction signals in correspondence with differences between said pulse-frequency signals.

2. An x-ray analysis apparatus as claimed in claim 1, further characterised in that the address-to-data conversion means comprises a pulse-shift-correction random-access memory.

3. An x-ray analysis apparatus as claimed in claim 2, further characterised in that said pulse-frequency signal comparison means comprises two frequency-to-amplitude converters, and a differential integrator.

4. An x-ray analysis apparatus as claimed in claim 2, further characterised in that said pulse-frequency signal comparison means comprises a first counter operating in an ascending counting direction, a second counter operating in a descending counting direction, and an integration circuit.

5. An x-ray analysis apparatus as claimed in claim 1, further characterised in that the address-to-data conversion means comprises a pulse-shift-correction memory.

6. An x-ray analysis apparatus as claimed in claim 5, further characterised in that said pulse-frequency signal comparison means comprises two frequency-to-amplitude converters, and a differential integrator.

7. An x-ray analysis apparatus as claimed in claim 5, further characterised in that said pulse-frequency signal comparison means comprises a first counter operating in an ascending counting direction, a second counter operating in a descending counting direction, and an integration circuit.

8. An x-ray analysis apparatus as claimed in claim 1, further characterised in that said pulse-frequency signal comparison means comprises two frequency-to-amplitude converters, and a differential integrator.

9. An x-ray analysis apparatus as claimed in claim 8, further characterised in that said pulse-frequency signal comparison means comprises a first counter operating in an ascending counting direction, a second counter operating in a descending counting direction, and an integration circuit.

10. An x-ray analysis apparatus as claimed in claim 9, further characterised in that the detector reading circuit means comprises a count rate switch for activating said pulse-frequency signal comparison means in dependence of said pulse-frequency signals exceeding a threshold.

11. An x-ray analysis apparatus as claimed in claim 8, further characterised in that the detector reading circuit means comprises a count rate switch for activating said pulse-frequency signal comparison means in dependence of said pulse-frequency signals exceeding a threshold.

12. An x-ray analysis apparatus as claimed in claim 1, further characterised in that said pulse-frequency signal comparison means comprises a first counter operating in an ascending counting direction, a second counter operating in a descending counting direction, and an integration circuit.

13. An x-ray analysis apparatus as claimed in claim 12, further characterised in that the detector reading circuit means comprises a count rate switch for activating said pulse-frequency signal comparison means in dependence of said pulse-frequency signals exceeding a threshold.

14. An x-ray analysis apparatus as claimed in claim 1 further characterised in that the detector reading circuit means comprises a count rate switch for activating said pulse-frequency signal comparison means in dependence of said pulse-frequency signals exceeding a threshold.

15. An x-ray analysis apparatus as claimed in claim 1, further characterised in that the analog-to-digital converter is a Flash-analog-to-digital converter.

16. A detector reading circuit means suited for application in an x-ray analysis apparatus having a detector for producing digital signals in correspondence with the energy of received x-ray photons, said detector reading circuit means comprising an address-to-data conversion means for receiving said digital signals as addresses and for producing pulse-frequency signals as data in response to said addresses, and pulse-frequency signal comparison means for producing correction signals in correspondence with difference between said pulse-frequency signals.

* * * * *